(12) United States Patent
Oppong et al.

(10) Patent No.: US 6,576,629 B1
(45) Date of Patent: Jun. 10, 2003

(54) MICROBICIDAL COMPOSITIONS AND METHODS USING COMBINATIONS OF PROPICONAZOLE AND N-ALKYL HETEROCYCLES AND SALTS THEREOF

(75) Inventors: David Oppong, Cordova, TN (US); Marilyn S. Whittemore, Memphis, TN (US); M. Sheldon Ellis, Cordova, TN (US); Robert H. Miller, Jr., Oakland, TN (US); Xiaugdong Zhou, Memphis, TN (US); Michael E. Elmore, Collierville, TN (US)

(73) Assignee: Buckman Laboratories International, Inc., Memphis, TN (US)

( * ) Notice: Subject to any disclaimer, the term of this patent is extended or adjusted under 35 U.S.C. 154(b) by 0 days.

(21) Appl. No.: 09/369,298

(22) Filed: Aug. 6, 1999

(51) Int. Cl.$^7$ .................. A61K 31/535; A61K 31/41; A01N 43/64
(52) U.S. Cl. ..................... 514/231.2; 514/383
(58) Field of Search ............... 514/383, 231.2

(56) References Cited

U.S. PATENT DOCUMENTS

| | | | |
|---|---|---|---|
| 3,923,870 A | 12/1975 | Singer | 260/482 |
| 4,945,109 A | 7/1990 | Rayudu | 514/478 |
| 5,200,421 A | 4/1993 | Ludwig et al. | 514/383 |
| 5,219,875 A | 6/1993 | Sherba et al. | 514/373 |
| 5,250,194 A | 10/1993 | Hollis et al. | 210/764 |
| 5,250,559 A | 10/1993 | Mittermeier et al. | 514/383 |
| 5,326,777 A | 7/1994 | Ludwig et al. | 514/383 |
| 5,328,926 A | 7/1994 | Oppong | 514/372 |
| 5,403,844 A | 4/1995 | Mittermeier et al. | 514/275 |
| 5,567,705 A | 10/1996 | Mittermeier et al. | 514/275 |
| 5,627,188 A | 5/1997 | Mittermeier et al. | 514/275 |
| 5,902,808 A | * 5/1999 | Whittemore et al. | 514/231.2 |
| 5,902,820 A | * 5/1999 | Jacquess et al. | 514/383 |

FOREIGN PATENT DOCUMENTS

| | | | |
|---|---|---|---|
| EP | 0897666 | * | 2/1999 |
| WO | WO 94/26112 | | 11/1994 |
| WO | WO 96/38042 | | 12/1996 |
| WO | 9638042 | * | 12/1996 |

OTHER PUBLICATIONS

The Pesticide Manual 855–57 (Clive Tomlin ed., British Crop Protection Council and Royal Society of Chemistry, 10th ed. 1994).

* cited by examiner

Primary Examiner—Alton N. Pryor
(74) Attorney, Agent, or Firm—Morgan, Lewis & Bockius LLP

(57) ABSTRACT

A method for increasing the effectiveness of the microbicide propiconazole, (RS)-1-2-[(2,4-dichlorophenyl)-2-propyl-1,3-dioxalan-2ylmethyl]-1H-1,2,4-triazole, is described. In the method, propiconazole and a potentiator, an N-alkyl heterocyclic compound, its salt, or a mixture thereof, are applied to a substrate or aqueous system subject to the growth of microorganisms. The N-alkyl heterocyclic compound, its salt, or a mixture thereof is applied in an amount effective to increase the microbicidal activity of the microbicide. The N-alkyl heterocyclic compound has the formula:

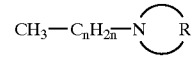

The variable "n" ranges from 5 to 17, and the heterocyclic ring defined by

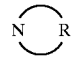

is a substituted or unsubstituted ring having four to eight members. Microbicidal compositions are described where propiconazole and an N-alkyl heterocyclic compound, its salt, or a mixture thereof are present in a combined amount effective to control the growth of at least one microorganism. Methods for controlling the growth of microorganisms on various substrates and in various aqueous systems are also described. The combination of propiconazole and an N-alkyl heterocyclic compound, its salt, or a mixture thereof is particularly useful as microbicidal in the leather industry, the lumber industry, the papermaking industry, the textile industry, the agricultural industry, and the coating industry, as well as in industrial process waters.

9 Claims, No Drawings

MICROBICIDAL COMPOSITIONS AND METHODS USING COMBINATIONS OF PROPICONAZOLE AND N-ALKYL HETEROCYCLES AND SALTS THEREOF

BACKGROUND OF THE INVENTION

1. Field of the Invention

The present invention relates to compositions and methods for controlling the growth of microorganisms on a variety of substrates and in aqueous systems. More particularly, the invention relates to a combination of propiconazole, also known as (RS)-1-2-[(2,4-dichlorophenyl)-4-propyl-1,3-dioxalan-2-ylmethyl]-1H-1,2,4-triazole, with an N-alkyl heterocyclic compound, its salt or a mixture thereof where the N-alkyl heterocyclic compound, its salt, or mixture thereof potentiates the microbicidal activity of propiconazole.

2. Background of the Invention

A large variety of commercial, industrial, agricultural, and wood materials or products are subject to microbiological attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as microbicides have been used to prevent microbiological deterioration of industrial systems, raw materials, and products. Examples of such microbicides include:

Kathon: a two component microbicide mixture of 5-chloro-2-methyl-4-isothiazolin-3-one (CMI) and 2-methyl-4-isothiazolin-3-one (MI). Kathon is a broad spectrum microbicide used in the pulp and paper industry. Kathon is also recommended to control bacteria and fungi in water-based paper coatings and coating components. Kathon is available from Rohm and Haas, Philadelphia Pa. and as Busan® 1078 from Buckman Laboratories, Memphis Tenn. Busan® 1078 contains 1.15% by weight of CMI and 0.35% by weight of MI as active ingredients. CMI and MI have the following chemical structures:

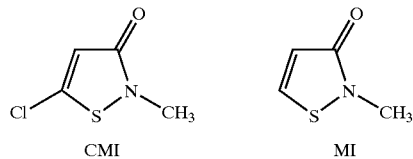

CMI       MI

Bronopol: 2-bromo-2-nitropropane-1,3-diol. Bronopol is available as MYACIDE® from ANGUS Chemical Company, Northbrook Ill. Bronopol is used in water treatment, oil production fluids, waste injection wells, and with pulp and paper. The chemical formula of bronopol is:

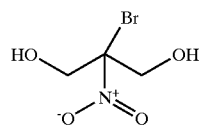

IPBC: Iodopropargyl butyl carbamate. IPBC can be obtained from Troy Chemical, Newark, N.J. IPBC is an effective fungicide, particularly in surface coating compositions, such as paint formulations. IPBC is disclosed in U.S. Pat. Nos. 3,923,870 and 5,219,875. IPBC has the following chemical formula:

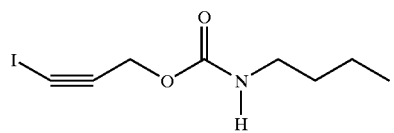

IPC: Iodopropargyl carbamate. IPC, an effective microbicide in aqueous systems and on numerous substrates, is disclosed in U.S. Pat. Nos. 4,945,109 and 5,328,926. The chemical formula of IPC is:

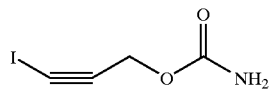

DBNPA: 2,2-Dibromo-3-nitrilopropionamide. DBNPA is available from Buckman Laboratories, Memphis, Tenn. as the product BUSAN® 94. DBNPA is a broad spectrum bactericide having particular use to control slime in the pulp and paper industry. BUSAN® 94 contains 20% by weight of DBNPA as its active ingredient. DBNPA has the chemical structure:

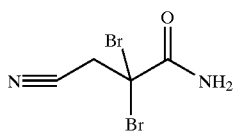

Tribromophenol: 2,4,6-Tribromophenol. Tribromophenol is an antifungal agent available from Great Lakes Chemical, West Lafayette, Ind. under the trade name GREAT LAKES PH-73. The chemical formula of tribromophenol is:

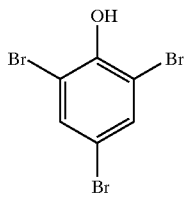

BIT: 1,2-benzisothiazoline-3-one. 1,2-Benzisothiazoline-3-one is a biocide useful for a variety of aqueous systems, such as metalworking fluids, paint, adhesives, starch-based-products, cellulose ether solutions, resin and rubber emulsions. 1,2-benzisothiazoline-3-one is available from ICI Specialty Chemicals, Melbourne, Australia as the product PROXEL GXL-20, an aqueous solution of dipropylene glycol 20% by weight of 1,2-benzisothiazoline-3-one as the active ingredient. 1,2-Benzisothiazoline-3-one has the following chemical structure:

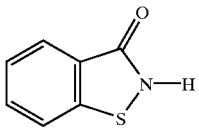

Propiconazole: (RS)-1-2-[(2,4-dichlorophenyl)-4-propyl-1,3-dioxalan-2-ylmethyl]-1H-1,2,4-triazole. Propiconazole is a known fungicide (U.S. Pat. Nos. 5,627,188, 5,567,705, 5,403,844, 5,326,777, 5,250,559 and 5,200,421). Propiconazole has the following chemical structure:

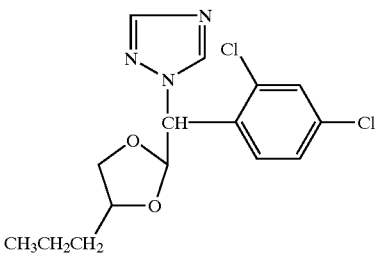

Despite the existence of such microbicides, industry is constantly seeking more cost-effective technology which offers equal or better protection at lower cost and lower concentration. The concentration of conventional microbicides and the corresponding treatment costs for such use, can be relatively high. Important factors in the search for cost-effective microbicides include the duration of microbicidal effect, the ease of use and the effectiveness of the microbicide per unit weight.

SUMMARY OF THE INVENTION

In view of industry's search for more cost effective microbicides, the invention offers an improvement over current products or practices. One embodiment of the invention relates to a method to increase the effectiveness of the microbicide propiconazole or (RS)-1-2-[(2,4-dichlorophenyl)-4-propyl-1,3-dioxalan-2ylmethyl]-1H-1,2,4-triazole. This method applies to a substrate or aqueous system subject to the growth of microorganisms a combination of propiconazole and a potentiator. The potentiator is an N-alkyl heterocyclic compound, its salt, or a mixture thereof and is present in an amount effective to potentiate or increase the microbicidal activity of propiconazole. The N-alkyl heterocyclic compound has the formula (I):

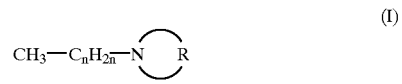

(I)

For the N-alkyl heterocyclic compound, n may vary from 5 to 17 and the heterocyclic ring defined by

is a substituted or unsubstituted ring having four to eight members. The combination of propiconazole with the potentiating N-alkyl heterocyclic compound, its salt or mixture thereof achieves superior microbicidal activity at lower concentrations and lower cost than propiconazole alone.

Another embodiment of the invention provides a microbicidal composition. The composition contains (a) propiconazole and (b) a potentiator. The potentiator is an N-alkyl heterocyclic compound of formula (I), as defined above, its salt or a mixture thereof. In the composition, propiconazole (a) and the potentiator (b) are present in a combined amount effective to control the growth of at least one microorganism.

Another embodiment of the invention provides a method for controlling the growth of a microorganism on a substrate. This method contacts a substrate susceptible to the growth of microorganisms with a microbidical composition containing propiconazole and a potentiator where the potentiator is an N-alkyl heterocyclic compound of formula (I), as defined above, its salt or a mixture thereof. The propiconazole and the potentiating N-alkyl heterocyclic compound, its salt, or a mixture thereof are present in a combined amount effective to control the growth of at least one microorganism on the substrate.

Another embodiment of the invention provides a method for controlling the growth of microorganisms in an aqueous system capable of supporting growth of a microorganism. This method treats the aqueous system with a microbicidal composition containing propiconazole and a potentiator. The potentiator is an N-alkyl heterocyclic compound of formula (I), as described above, its salt or a mixture thereof. Propiconazole and the potentiator or the N-alkyl heterocyclic compound, its salt, or a mixture thereof are present in a combined amount effective to control the growth of at least one microorganism in the aqueous system.

According to the invention, the combination of propiconazole and a potentiator such as an N-alkyl heterocyclic compound, its salt, or a mixture thereof is useful in preventing the microbiological attack, degradation, or deterioration of various types of raw materials and products such as leather, textiles, pulp, paper and paperboard, coatings, lumber, as well as agricultural products such as seeds and crops. Advantageously, the combination may be used in various industrial processes used to prepare or manufacture these products. Accordingly, additional embodiments of the invention employ the combination to control the growth of microorganisms on or in such industrial products, raw materials or processes.

The foregoing and other features and advantages of the invention will be made more apparent from the following detailed description and preferred embodiments.

DETAILED DESCRIPTION OF THE INVENTION

The invention relates to a method to increase the effectiveness of a microbicide. The microbicide as used in the invention may not only kill microorganisms but may also suppress the growth of such microorganisms. The method according to the invention applies propiconazole and a potentiator to a substrate or aqueous system subject to the growth of microorganisms. The combination of propiconazole and a potentiator achieves superior microbicidal activity at lower propiconazole concentrations as compared to the microbicidal capability of propiconazole alone. According to the invention, the potentiator is an N-alkyl heterocyclic compound, its salt, or a mixture thereof and is present in the combination in an amount effective to increase the microbicidal activity of propiconazole.

According to the invention, the combination of propiconazole and an N-alkyl heterocyclic compound, its salt, or a mixture thereof demonstrates an unexpected, enhanced microbicidal effect. The combination may have a microbicidal effect or an antimicrobic effect. Preferably, the combination has a microbicidal effect. The combination of propiconazole and an N-alkyl heterocyclic compound, its salt, or a mixture thereof achieves superior microbicidal activity at lower propiconazole concentrations as compared to the microbicidal capability of propiconazole alone. Thus, the N-alkyl heterocyclic compound, its salt, or a mixture thereof is said to potentiate the microbicidal activity of propiconazole. Such a superior effect presents a distinct economic advantage and increases propiconazole's effectiveness per unit weight.

According to the invention, an N-alkyl heterocyclic compound, its salt, or a mixture thereof may be used as a potentiator to increase the effectiveness of propiconazole alone or a mixture of propiconazole and other microbicides such as, for example, sodium 2-mercaptobenzothiazole, 5-chloro-2-methyl-4-isothiazolin-3-one, 2-methyl-4-isothiazolin-3-one, 2-bromo-2-nitropropane-1,3-diol, iodopropargyl butyl carbamate, iodopropargyl carbamate, iodopropargyl alcohol, 2,2-dibromo-3-nitrilopropionamide, tribromophenol, 1,2-benzisothiazoline-3-one, bis(trichloromethyl)sulfone, N-alkyldimethylbenzyl ammonium chloride, and mixtures thereof. The N-alkyl heterocyclic compound, its salt, or a mixture of N-alkyl heterocyclic compounds or salts thereof, may be used with and in the same manner as propiconazole is used. Preferably, one or more N-alkyl heterocyclic compounds or salts thereof are incorporated into the propiconazole formulation.

In one embodiment, the invention relates to a microbicidal composition containing propiconazole and a potentiator of at least one N-alkyl heterocyclic compound, its salt, or a mixture thereof as described above. Propiconazole and the potentiator are present in a combined amount effective to control the growth of at least one microorganism.

The N-alkyl heterocyclic compound employed in the invention has the following formula:

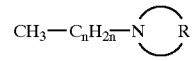

The variable "n" may vary from 5 to 17, and preferably from 7 to 15. Most preferably, n is 7 or 11. The alkyl chain defined by $CH_3C_nH_{2n}$— may be branched or unbranched. Branched alkyl chains may lose some of their solubility in water or other aqueous systems. Unbranched alkyl groups are generally preferred.

The heterocyclic ring defined by

may have four to eight members and is preferably a five-, six-, seven-, or eight-membered ring. Most preferably the heterocyclic ring is a six-membered ring. Although the heterocyclic ring always contains one nitrogen atom, the remainder is generally a carbocycle. However, the ring may contain one or more additional heteroatoms selected from N, O, or S. The ring may be saturated or unsaturated. The ring may also have common substituents such as alkyl groups, substituted alkyl groups, alkenyl groups, substituted alkenyl groups, amino groups, an oxo group to form a carbonyl group, halogens, etc. The heterocyclic ring may also be part of a multiple ring structure.

The heterocycles listed below exemplify substituted or unsubstituted heterocyclic rings which may be used in the N-alkyl heterocyclic compounds utilized in preferred embodiments of the invention. Examples of five-membered heterocyclic rings include, but are not limited to, pyrrolidinyl, 2-pyrrolidinonyl, pyrrolinyl, pyrazolidinyl, pyrazolinyl, pyrazolyl, imidazolidinyl, imidazolinyl, imidazolyl and oxazolidinyl. Six-membered rings include, but are not limited to, piperidinyl, piperazinyl, and morpholinyl. Seven- and eight-membered rings such as hexamethyleneiminyl and heptamethyleneiminyl may also be used in the invention. One of ordinary skill will appreciate that other heterocyclic rings may also be used.

Salts of N-alkyl heterocyclic compounds, including those described above, may also be used in the present invention. Such salts are formed at the nitrogen moiety of the N-alkyl heterocyclic compound (referred to as "quaternized N-alkyl heterocyclic salts") and have the general formula

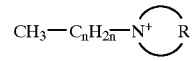

where n and

are as defined above. Preferably, the salts of the N-alkyl heterocyclic compounds are acid salts such as, for example, $C_1$–$C_{10}$ carboxylic acid salts. More preferably, the salt of the N-alkyl heterocyclic compound is a formic acid salt.

N-alkyl heterocyclic compounds or salts thereof useful in the invention are available either commercially from chemical supply houses or may be prepared from starting materials using well-known literature methods. U.S. Pat. No. 5,250,194 discloses exemplary methods and is incorporated herein by reference.

U.S. Pat. No. 5,250,194 also describes N-dodecyl heterocyclic compounds and their use as microbicides for aqueous systems to inhibit the growth of microorganisms, the formation of slime in aqueous systems, or the disfigurement or deterioration of substances susceptible to microbiological growth. One example of an N-alkyl heterocyclic compound useful as such a microbicide is N-dodecyl morpholine (DDM). DDM is manufactured by BASF GmbH and by Buckman Laboratories International Inc., Memphis, Tenn.

Preferred N-alkyl heterocyclic compounds for use in the invention include N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine, N-dodecyl-2-methyl-piperidine, 2-N-octylisothiazoline-3-one, and 4,5-dichloro-2-N-octyl-4-isothiazolin-3-one. Most preferred of these compounds are N-dodecyl morpholine, (DDM), and N-dodecyl imidazole, (DDI).

Depending on the application, microbicidal compositions according to the invention may be prepared in various forms known in the art. For example, the composition may be prepared in liquid form as an aqueous solution, dispersion, emulsion, or suspension, a dispersion or suspension in a non-solvent, or as a solution by dissolving propiconazole and the N-alkyl heterocyclic compound, its salt, or a mixture thereof in a solvent or combination of solvents. Suitable solvents include, but are not limited to, methyl ethers of glycols, M-pyrol or 1-methyl-pyrrolidinone, or petroleum distillates. The microbicidal composition may be prepared as a concentrate for dilution prior to its intended use. Common additives such as surfactants, emulsifiers, dispersants, and the like may be used as known in the art to increase the solubility of propiconazole or the N-alkyl heterocyclic compound or salt thereof in a liquid composition or system, such as an aqueous composition or system. In many cases, the microbicidal composition of the invention may be solubilized by simple agitation.

Microbicidal compositions of the invention may also be prepared in solid form, for example as a powder or tablet, using means known in the art. In a preferred method of preparation, a liquid product containing propiconazole is deposited on a carrier such as diatomaceous earth or kaolin and mixed with an N-alkyl heterocyclic compound, its salt, or a mixture thereof in the form of a liquid or solution to form a powder or tablet.

The propiconazole and the N-alkyl heterocyclic compound, its salt or a mixture thereof may be combined in a single composition. Alternatively, the propiconazole and the N-alkyl heterocyclic compound, its salt or a mixture thereof may be employed as separate components such that combined amount for the intended use is effective to control the growth of at least one microorganism.

As discussed above, according to the invention, the N-alkyl heterocyclic compound, its salt or a mixture thereof potentiates the microbicidal effect of propiconazole. Thus, combining an N-alkyl heterocyclic compound, its salt, or a mixture thereof with propiconazole provides superior microbicidal activity to control the growth of microorganisms as compared to the microbicidal capability of the propiconazole alone.

According to the invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The combination of propiconazole and a potentiator, an N-alkyl heterocyclic compound, its salt, or a mixture thereof, described here can, in many cases, reduce the total microbiological count to undetectable limits and maintain the count at that level for a significant period of time. Accordingly, the combination may be used to preserve a substrate or system.

The effective amount or percentage of the combination of propiconazole and an potentiator of an N-alkyl heterocyclic compound, its salt, or a mixture thereof necessary to achieve the desired result will vary somewhat depending on the substrate or aqueous system to be protected, the conditions for microbial growth, the particular microbicide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 1.0% or about 10,000 ppm. With aqueous systems, an effective amount may range from about 0.5 to about 10,000 parts per million, more preferably from about 5 to about 5000 parts per million of the aqueous system, and most preferably from, about 10 to about 1000 parts per million. Similar amounts effectively control slime formation. For slime control, effective amounts preferably range from about 1 to about 1000 parts per million, and more preferably, from about 1 to about 200 parts per million of the aqueous system.

In a preferred embodiment, combinations of propiconazole and an N-alkyl heterocyclic compound, its salt, or a mixture thereof are those combinations having a weight ratio of propiconazole to an N-alkyl heterocyclic compound, its salt, or a mixture thereof from about 99:1 to about 1:99. More preferably the weight ratio is from about 60:10 to about 10:60, and most preferably, from about 50:50 to about 25:75. The weight ratio may vary depending on the microbicide, the intended use, the microorganism encountered as well as the particular material, product, or system to which the combination according to the invention is applied.

The combination of propiconazole and an N-alkyl heterocyclic compound, its salt, or a mixture thereof may be applied in a variety of industrial uses and processes for microorganism control. The combination may be used with or in place of and in the same manner as other microbicides traditionally used in the particular industry. As discussed above, such industries include, but are not limited to the leather industry, the lumber industry, the papermaking industry, the textile industry, the agricultural industry, and the coating industry. The combination of propiconazole and an N-alkyl heterocyclic compound, its salt, or a mixture thereof may also be used with aqueous systems such as those previously discussed which are subject to microbiological attack and degradation. The problems caused by microbiological attack and deterioration in these various applications has been described above. The use of the combination of propiconazole and an N-alkyl heterocyclic compound, its salt, or a mixture thereof according to the invention to control the growth of microorganisms in particular exemplary applications is described below.

The invention also relates to a method for controlling the growth of microorganisms on various substrates. The method comprises the step of contacting a substrate susceptible to microbiological growth or attack with propiconazole and an N-alkyl heterocyclic compound, its salt, or a mixture thereof, as described above. Propiconazole and an N-alkyl heterocyclic compound, its salt, or a mixture thereof are present in a combined amount effective to control the growth of at least one microorganism on the substrate. Preferably, the method may be used to eliminate or prevent substantially all microbiological growth on the substrate. As discussed above, propiconazole and the N-alkyl heterocyclic compound, its salt, or a mixture thereof may be applied together or as separate compositions. The amount of N-alkyl heterocyclic compound, its salt or mixture thereof used potentiates the microbicidal or antimicrobic activity of propiconazole. Preferred applications of this general method are discussed below.

In the leather industry, the combination of propiconazole and an N-alkyl heterocyclic compound, its salt, or a mixture thereof may be used to control the growth of microorganisms on a hide during a tanning process. To achieve this control, the hide is contacted with a combined amount of propiconazole and an N-alkyl heterocyclic compound, its salt, or a mixture thereof effective to control the growth of at least one microorganism on the hide. The combination of propiconazole and the N-alkyl heterocyclic compound, its salt, or a mixture thereof may be used in the tanning process in similar amounts and manner similar to that used to apply other microbicides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fat liquoring stage. The combination of propiconazole and an N-alkyl heterocyclic compound, its salt, or a mixture thereof may be used during all process stages in the tanning process in addition to those stages where a known microbiological problem is occurring. In each stage, the combination of propiconazole and an N-alkyl heterocyclic compound, its salt, or a mixture thereof may be a component of the appropriate tanning liquor applied to the hide undergoing tanning.

Incorporating propiconazole and an N-alkyl heterocyclic compound, its salt, or a mixture thereof in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retanning liquor, a dye liquor, and a fat liquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a combination of propiconazole and an N-alkyl heterocyclic compound, its salt, or a mixture thereof according to the invention effectively controls the growth of a microorganism on the textile substrate. In a textile process, the combination may be used in similar amounts and a manner similar to other antimicrobial compounds commonly used in such processes. As one of ordinary skill would appreciate, particular amounts generally depend on the textile substrate and the degree of microbiological resistance required.

The step of contacting the textile substrate with the combination of propiconazole and an N-alkyl heterocyclic compound, its salt, or a mixture thereof may be accomplished using means known in the textile art. To control microbiological growth, a textile process generally dips the textile substrate into a bath containing a microbicide alone or with other chemicals used to treat the textile substrate. Alternatively, the textile substrate may be sprayed with a formulation containing a microbicide. In the bath or the spray, the combination of propiconazole and N-alkyl heterocyclic compound, its salt, or a mixture thereof according to the invention are present in a combined amount effective to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation of lumber. The combination of propiconazole and an N-alkyl heterocyclic compound, its salt, or a mixture thereof according to the invention is effective to control the growth of microorganisms on lumber.

The combination of propiconazole and an N-alkyl heterocyclic compound, its salt, or a mixture thereof may be used to protect the lumber in similar amounts and a similar manner employed for other microbicides used in the lumber industry. Contacting lumber with an effective amount of the combination may be accomplished, for example, by spraying the lumber with an aqueous formulation containing the combination of propiconazole and an N-alkyl heterocyclic compound, its salt, or a mixture thereof, by dipping the lumber into a dip bath containing the combination, or other means known in the art. Dipping the lumber in an aqueous bath is preferred.

Propiconazole and the N-alkyl heterocyclic compound, its salt, or a mixture thereof are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the microbicide, the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the microbicidal combination.

The combination of propiconazole and an N-alkyl heterocyclic compound, its salt, or a mixture thereof according to the invention also has uses in the agricultural industry. To control the growth of microorganisms on a seed or plant, the seed or plant may be contacted with propiconazole and an N-alkyl heterocyclic compound, its salt, or a mixture thereof in a combined amount effective to control the growth of at least one microorganism on the seed or plant. This contacting step may be accomplished using means and amounts known in the agricultural industry for other microbicides. For example, the seed or plant may be sprayed with an aqueous formulation containing the combination of propiconazole and an N-alkyl heterocyclic compound, its salt, or a mixture thereof, or dipped into a bath containing the combination. After being sprayed or dipped, the seed or plant is generally dried by means known in the art such as drip drying, heated drying, or air drying. For plants or crops, the combination may also be applied using a soil drench. Soil drenching is particularly advantageous when the microorganisms of concern inhabit the soil surrounding the plant.

Yet another aspect of the invention is a method for controlling the growth of microorganisms in an aqueous system capable of supporting such growth. The aqueous system is treated with propiconazole and an N-alkyl heterocyclic compound, its salt, or a mixture thereof such that the propiconazole and the N-alkyl heterocyclic compound, its salt, or a mixture thereof are present in a combined amount effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (both intake cooling water and effluent cooling water), and waste waters including waste waters or sanitation waters undergoing treatment of the waste in the water, e.g. sewage treatment.

As with the other uses discussed above, the combination of the invention may be used in the same amounts and in the same manner as microbicides traditionally used in these various aqueous systems. The combination not only protects the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the invention is a method for controlling the growth of microorganisms on paper or in a papermaking process, e.g., in a pulp or paper slurry and on a finished paper product such as paper board. The paper, pulp, or slurry is contacted with propiconazole and an N-alkyl heterocyclic compound, its salt, or a mixture thereof in a combined amount effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with the combination of propiconazole and an N-alkyl heterocyclic compound, its salt, or a mixture thereof by spraying an aqueous dispersion containing the propiconazole and N-alkyl heterocyclic compound, its salt, or a mixture thereof onto the pulp after the pulp leaves the presses in a papermaking process. Or, the propiconazole and N-alkyl heterocyclic compound, its salt, or a mixture thereof may be incorporated into a bath used at the wet or size press and the web contacted by nipping the web to incorporate the combination into the web with any other agents applied at the press. Alternatively, the pulp may be contacted by mixing the propiconazole and N-alkyl heterocyclic compound, its salt, or a mixture thereof into the pulp/white water mixture, preferably prior to the pulp reaching the formation wire.

When treating paper (which includes paperboard and other cellulosic products or substrates), the propiconazole and N-alkyl heterocyclic compound, its salt, or a mixture thereof may be added into pulp slurries in the headbox, in the substrate forming solution, or in the white water system to treat the water system itself or for incorporation into the body of the paper. Alternatively, as with other known microbicides, the combination of propiconazole and an N-alkyl heterocyclic compound, its salt, or a mixture thereof according to the invention may be mixed into a coating used to coat the finished paper.

The activity of the combinations described above has been confirmed using standard laboratory techniques as discussed below. In many cases, the N-alkyl heterocyclic compound, its salt, or a mixture thereof potentiates the microbicidal effect of the propiconazole. The following examples are intended to illustrate, not limit, the invention.

EXAMPLES

Examples 1–4 illustrate potentiation of propiconazole by DDM. Each formulation was tested against various fungi according to ASTM E599-84 with an inoculum of approximately $10^6$ spores/mL.

Example 1

Minimum Inhibitory Concentration (MIC) in ppm against *A. Niger* in pulp substrate at pH 5

| Formulation | % Propiconazole | MIC of Formulation | MIC of Propiconazole |
|---|---|---|---|
| BUSAN ® 1292[1] | 24.7 | 320 | 80 |
| Pzole/DDM[2] | 10 | 200 | 20 |

[1]BUSAN ® 1292 is an emulsifiable concentrate available from Buckman Laboratories, Inc. containing propiconazole (24.7%), emulsifiers, and water
[2]Pzole/DDM: 10% Propiconazole, 40% Dodecylmorpholine (DDM)

Example 2

Minimum Inhibitory Concentration (MIC) in ppm against *A. Niger* in pulp substrate at pH 8

| Formulation | % Propiconazole | MIC of Formulation | MIC of Propiconazole |
|---|---|---|---|
| BUSAN ® 1292[1] | 24.7 | 320 | 80 |
| Pzole/DDM[2] | 10 | 400 | 40 |

[1]BUSAN ® 1292: is an emulsifiable concentrate available from Buckman Laboratories, Inc. containing propiconazole (24.7%), emulsifiers, and water
[2]Pzole/DDM: 10% Propiconazole, 40% Dodecylmorpholine (DDM)

Example 3

Minimum Inhibitory Concentration (MIC) in ppm against *Chaetomium globsum* in pulp substrate at pH 5

| Formulation | % Propiconazole | MIC of Formulation | MIC of Propiconazole |
|---|---|---|---|
| BUSAN ® 1292[1] | 24.7 | 80 | 20 |
| Pzole/DDM[2] | 10 | 50 | 5 |

[1]BUSAN ® 1292: is an emulsifiable concentrate available from Buckman Laboratories, Inc. containing propiconazole (24.7%), emulsifiers, and water
[2]Pzole/DDM: 10% Propiconazole, 40% Dodecylmorpholine (DDM)

Example 4

Minimum Inhibitory Concentration (MIC) in ppm against *Aspergillus terreus* in pulp substrate at pH 5

| Formulation | % Propiconazole | MIC of Formulation | MIC of Propiconazole |
|---|---|---|---|
| BUSAN ® 1292[1] | 24.7 | 320 | 80 |
| Pzole/DDM[2] | 10 | 400 | 40 |

[1]BUSAN ® 1292: is an emulsifiable concentrate available from Buckman Laboratories, Inc. containing propiconazole (24.7%), emulsifiers, and water
[2]Pzole/DDM: 10% Propiconazole, 40% Dodecylmorpholine (DDM)

Example 5

Separate Addition of Propiconazole and Potentiator: Anti-sapstain Field Trials. Combinations of Propiconazole and Dodecyl Morpholine (DDM) to effectively control the Growth of Microorganisms on wood.

Treatment Method

Several dilutions of propiconazole formulations containing either propiconazole alone as the active ingredient or a tank-mix combination of propiconazole and the potentiator dodecylmorpholine (DDM) were investigated with respect to their ability to prevent the formation of mold, sapstain, and decay on wood. Sections (1"×6"×12") of freshly cut sapwood from Southern Yellow Pine (*Pinus palustris*) were prepared just prior to treatment. The wood specimens were arranged into stacks of twelve pieces with each stack serving as the complete unit or packet per each chemical formulation within the treatment protocol. The two end pieces of each stack serve as an "end" or "buffer" zone. Only the middle ten sections will actually by evaluated. Individual sections are marked with a pencil for treatment identification.

Aqueous suspensions of propiconazole formulations were prepared using five gallon plastic containers. First water was added to the five gallon container to a prescribed mark on the side of the container. Next depending upon the desired concentration, a sufficient quantity of a propiconazole containing formulation was added. Next, if desired, the potentiator DDM is added separately just prior to use followed by stirring to achieve adequate mixing.

Each stack (12 pieces) of sapwood is treated by manually submerging the stack into the aqueous propiconazole and/or, potentiator treatment suspension. The pieces are slightly agitated in order to completely surround each piece with the suspension. After one minute the wood is removed from the treatment container, excess solution is drained briefly, and then the stack is set aside for one day to air dry.

The stacks of dry, treated sapwood are then placed side by side outdoors across two long pieces of board to raise the treated stacks slightly above the ground. The wood stacks are then as a group covered with black (opaque) plastic in order to protect the wood from rain (chemical leaching), direct exposure to light (photodegradation of the chemical formulation), and to serve as a humidity chamber. The wood stacks were evaluated three and six weeks for stain, mold, and decay after treatment.

Evaluation Method

At the three week point and at the six week point, the plastic cover was removed and each stack was withdrawn one at a time for easier handling. For each stack, each of the ten middle sections were individually examined and an estimate of the percentage of the surface area of each section infested with sapstain (the stain is typically bluish purple) was recorded. The stack was then returned to its original position before the next stack was withdrawn for evaluation. Once all evaluations had been completed, the plastic cover was replaced and secured for further incubation if desired.

TABLE 5a

Sapstain Trials. Southern Yellow Pine Treated at pH 5. 12 Boards per treatment.

| Treatment | Product A | Active Ingredient (a.i.) in A | % a.i. in A | ppm a.i. solution | Amount of Product A added (mL) | Product B | Potentiator in B | % Potentiator in B | ppm Potentiator in solution | Amount of Product B added (mL) | Average % Stain and Mold after 6 weeks |
|---|---|---|---|---|---|---|---|---|---|---|---|
| C1 | BUSAN ® | Propiconazole | 23.6 | 250 | 11 | — | — | — | — | — | 7.13 |
| C2 | 1292* | | | 500 | 10 | | | | | | 7.68 |
| C3 | | | | 750 | 10 | | | | | | 7.95 |
| C4 | | | | 1000 | 11 | | | | | | 8.63 |
| E1 | BUSAN ® | Propiconazole | 23.6 | 300 | 13 | BSP ® | DDM* | 30 | 2000 | 50 | 8.96 |
| E2 | 1292* | | | 450 | 6 | 2181 | | | | | 9.50 |
| E3 | | | | 600 | 6 | | | | | | 7.86 |
| E4 | | | | 750 | 7 | | | | | | 8.63 |
| F1 | BUSAN ® | Propiconazole | 23.6 | 300 | 13 | BSP ® | DDM* | 30 | 1000 | 33 | 8.30 |
| F2 | 1292* | | | 450 | 6 | 2181 | | | | | 8.65 |
| F3 | | | | 600 | 6 | | | | | | 7.80 |
| F4 | | | | 750 | 7 | | | | | | 8.23 |

*BUSAN ® 1292 is an emulsifiable concentrate available from Buckman Laboratories, Inc. containing propiconazole (23.6%), emulsifiers, and water;
**DDM: Dodecyl morpholine TABLE 5b Sapstain Trials. Southern Yellow Pine Treated at pH 5. 12 Boards per treatment

| Treatment | Product A | Active Ingredient (a.i.) in A | % a.i. in A | ppm a.i. solution | Amount of Product A added (mL) | Product B | Potentiator in B | % Potentiator in B | ppm Potentiator in solution | Amount of Product B added (ppm potentiator) | Average % Stain and Mold after 6 weeks |
|---|---|---|---|---|---|---|---|---|---|---|---|
| G1 | BUSAN ® | Propiconazole | 23.6 | 250 | 10.59 | — | — | — | — | — | 6.00 |
| G2 | 1292* | | | 500 | 21.19 | | | | | | 6.04 |
| G3 | | | | 750 | 31.85 | | | | | | 6.83 |
| G4 | | | | 1000 | 42.37 | | | | | | 7.00 |
| H1 | BUSAN ® | Propiconazole | 23.6 | 750 | 31.85 | BSP ® | DDM*** | 60 | 2000 | 1250 | 7.67 |
| H2 | 1292* | | | 750 | 31.85 | 2180** | | | | 2500 | 7.48 |
| H3 | | | | 750 | 31.85 | | | | | 3787 | 8.63 |
| H4 | | | | 750 | 31.85 | | | | | 5000 | 8.25 |
| I1 | BUSAN ® | Propiconazole | 23.6 | 500 | 21.19 | BSP ® | DDM*** | 60 | 1000 | 1250 | 7.63 |
| I2 | 1292* | | | 500 | 21.19 | 2180** | | | | 2500 | 6.75 |
| I3 | | | | 500 | 21.19 | | | | | 3787 | 6.88 |
| I4 | | | | 500 | 21.19 | | | | | 5000 | 7.88 |

*BUSAN ® 1292 is an emulsifiable concentrate available from Buckman Laboratories, Inc. containing propiconazole (23.6%), emulsifiers and water;
**BSP ® 2180 is Busperse 2180 contains 60% DDM and is available from Buckman Laboratories, Inc.;
***DDM: Dodecyl morpholine Example 6

Single Formulation of Propiconazole/Potentiator: Antisapstain Field Trials. Combinations of Propiconazole and Dodecyl Morpholine (DDM) to effectively control the Growth of Microorganisms on wood.
Treatment Method Several dilutions of formulations containing both propiconazole, as the active ingredient, and the potentiator dodecylmorpholine (DDM) were investigated with respect to their ability to prevent the formation of mold, sapstain, and decay on wood. Dilutions of formulations without the potentiator were included in the study as controls. Sections (1"×6"×12") of freshly cut sapwood from Southern Yellow Pine (*Pinus palustris*) were prepared just prior to treatment. The wood specimens were arranged into stacks of twelve pieces with each stack serving as the complete unit or packet per each chemical formulation within the treatment protocol. The two end pieces of each stack serve as an "end" or "buffer" zone. Only the middle ten sections will actually by evaluated. Individual sections are marked with a pencil for treatment identification.

Aqueous suspensions of propiconazole formulations were prepared using five gallon plastic containers. First water was added to the five gallon container to a prescribed mark on the side of the container. Next depending upon the desired concentration, a sufficient quantity of a propiconazole and DDM containing formulation was added. Optionally, a surfactant may also be added to the formulation.

Each stack (12 pieces) of sapwood is treated by manually submerging the stack into the aqueous propiconazole and/or potentiator treatment suspension. The pieces are slightly agitated in order to completely surround each piece with the suspension. After one minute the wood is removed from the treatment container, excess solution is drained briefly, and then the stack is set aside for one day to air dry.

The stacks of dry, treated sapwood are then placed side by side outdoors across two long pieces of board to raise the treated stacks slightly above the ground. The wood stacks are then as a group covered with black (opaque) plastic in order to protect the wood from rain (chemical leaching), direct exposure to light (photodegradation of the chemical formulation), and to serve as a humidity chamber. The wood stacks were evaluated three and six weeks for stain, mold, and decay after treatment.
Evaluation Method At the three week point and at the six week point, the plastic cover is removed and each stack is withdrawn one at a time for easier handling. For each stack, each of the ten middle sections are individually examined and an estimate of the percentage of the surface area of each section infested with sapstain (the stain is typically bluish purple) is recorded. The stack is then returned to its original position before the next stack is withdrawn for evaluation. Once all evaluations have been completed, the plastic cover is replaced and secured for further incubation if desired.

TABLE 6

Sapstain Trials. Southern Yellow Pine Treated at pH 5. 12 Boards per treatment

| Treatment | Formulation | % Propiconazole in formulation | % Potentiator DDM** in formulation | % Ethoxylated Castor Oil in formulation | Propiconazole (ppm in solution) | Amount of Formulation Added (mL) | Average % Stain and Mold after 6 weeks |
|---|---|---|---|---|---|---|---|
| G1 | BUSAN ® | 23.6 | 0 | 0 | 250 | 10.59 | 7.00 |
| G2 | 1292* | | | | 500 | 21.19 | 6.83 |
| G3 | | | | | 750 | 31.85 | 6.04 |
| G4 | | | | | 1000 | 42.37 | 6.00 |
| D1 | C[3] | 10 | 40 | 0 | 250 | 25.00 | 7.04 |
| D2 | | | | | 500 | 50.00 | 6.383 |
| D3 | | | | | 750 | 75.19 | 5.79 |

TABLE 6-continued

Sapstain Trials. Southern Yellow Pine Treated at pH 5. 12 Boards per treatment

| Treatment | Formulation | % Propiconazole in formulation | % Potentiator DDM** in formulation | % Ethoxylated Castor Oil in formulation | Propiconazole (ppm in solution) | Amount of Formulation Added (mL) | Average % Stain and Mold after 6 weeks |
|---|---|---|---|---|---|---|---|
| D4 | C[3] | 10 | 40 | 0 | 1000 | 100.0 | 5.50 |
| E1 | D[4] | 10 | 40 | 10 | 250 | 25.00 | 8.00 |
| E2 | | | | | 500 | 50.00 | 7.83 |
| E3 | | | | | 750 | 75.19 | 7.46 |
| E4 | | | | | 1000 | 100.0 | 6.75 |

*BUSAN ® 1292 is an emulsifiable concentrate available from Buckman Laboratories, Inc. containing propiconazole (23.6%), emulsifiers, and water
**DDM: Dodecyl morpholine
[3]Formulation C contains Busperse 2180 (contains 60% DDM, available from Buckman Laboratories, Inc.), propiconazole, and emulsifiers.
[4]Formulation D contains Busperse 2180 (contains 60% DDM, available from Buckman Laboratories, Inc.), propiconazole, surfactant and emulsifiers.

Example 7

Application of Combinations of Propiconazole and Dodecyl Morpholine in the Treatment of Leather Treatment Method Several dilutions of formulations containing both propiconazole, as the active ingredient, and the potentiator, dodecylmorpholine (DDM), were investigated with respect to their ability to prevent the formation of fungal growth in leather. Dilutions of formulations without the potentiator were included in the study as controls in addition to the control containing no active ingredient.

Pre-pickled hides were placed in a drum to which was then added water having a temperature of 78–82° F. and 6% sodium chloride (NaCl). The drum was started and allowed to run for 15 minutes. Next 0.3% formic acid diluted 1:10 in water was added to the drum which was then run for 30 minutes. Afterwards, 0.8% sulfuric acid diluted 1:15 in water was added to the drum. After running the drum for 2.5 hours, the drum was stopped and the pH of the float was taken and found to be between 1.8–2.2. The color of the cut of the leather was also checked with Bromocresol Green dye which ideally was yellow to very light green. Next a solution of 3% CHROMOSAL B (available from Bayer Co. containing 25% $Cr_2O_3$ and having 33% basicity) was added to the drum. Once the drum was started, a formulation containing either propiconazole or both propiconazole and dodecyl morpholine was then added. After 3 hours, 5% BAYCHROME A (available from Bayer Co. containing 23% $Cr_2O_3$ and having 66% basicity) was added to the drum which was then allowed to run overnight. Next the chrome penetration in the hides was evaluated visually. If chrome penetration was not sufficient, the drum was allowed to run for a longer period of time until sufficient chrome penetration was achieved. Once achieved, a basification process was begun by very slowly adding a solution of 1.7% sodium bicarbonate to the drum of which the heaters were turned on to increase the temperature within the drum. The sodium bicarbonate addition was added at such a rate as to not be completed under an hour. After sodium bicarbonate addition was complete, the drum was then run for 4 hours. After 4 hours, the pH of the float was checked. If the pH was between 3.65 and 3.85, the float was drained and the leather was washed with cold water. If the pH was lower than 3.65, additional sodium bicarbonate was added and the drum was run for another hour. The pH was again tested. If the pH was still too low, the process of adding sodium bicarbonate and running the drum was repeated until the pH fell within the desired range of 3.65 and 3.85.

Evaluation Method

Once a week for nine weeks, leather having been treated with propiconazole and a propiconazole/dodecyl morpholine combination was evaluated for growth of fungi. Evaluations were made for both the grain and the flesh surface of the leather based on the following scale:

| | |
|---|---|
| 10 | No Growth |
| 9 | |
| 8 | Slight Growth |
| 7 | |
| 6 | Medium Growth |
| 5 | |
| 4 | Moderately Heavy Growth |
| 3 | |
| 2 | Heavy Growth |
| 1 | |
| 0 | Completely Covered |

TABLE 7

Evaluation of Leather Subjected to Tropical Chamber After Treatment with Propiconazole and/or Dodecyl Morpholine (DDM)

| Main Components In Formulation | Dosage (%) | 1 Week G/F* | 2 Week G/F* | 3 Week G/F* | 4 Week G/F* | 5 Week G/F* | 6 Week G/F* | 7 Week G/F* | 8 Week G/F* | 9 Week G/F* |
|---|---|---|---|---|---|---|---|---|---|---|
| Control - No active agent | 0 | 10/10 | 2/4 | 0 | 0 | 0 | 0 | 0 | 0 | 0 |
| Prosan 24 (Psn 24)** 25% Propiconazole | 0.05% | 10/10 | 10/10 | 10/10 | 9/9 | 7/8 | 5/5 | 5/4 | 2/0 | 0 |

TABLE 7-continued

Evaluation of Leather Subjected to Tropical Chamber After Treatment with Propiconazole and/or Dodecyl Morpholine (DDM)

| Main Components In Formulation | Dosage (%) | 1 Week G/F* | 2 Week G/F* | 3 Week G/F* | 4 Week G/F* | 5 Week G/F* | 6 Week G/F* | 7 Week G/F* | 8 Week G/F* | 9 Week G/F* |
|---|---|---|---|---|---|---|---|---|---|---|
| Prosan 24** 25% Propiconazole | 0.10% | 10/10 | 10/10 | 10/10 | 9/9 | 8/5 | 7/2 | 5/2 | 5/2 | 0 |
| Prosan 24** 25% Propiconazole | 0.14% | 10/10 | 10/10 | 10/10 | 10/10 | 10/10 | 9/10 | 9/9 | 8/9 | 8/8 |
| Bsp 2180*** 60% DDM | 0.05% | 10/10 | 10/10 | 10/10 | 9/9 | 4/2 | 0 | 0 | 0 | 0 |
| Bsp 2180*** + Psn 24** 60% DDM + 25% Propiconazole | 0.05 + 0.05% | 10/10 | 10/10 | 10/10 | 9/10 | 8/9 | 5/8 | 4/8 | 2/5 | 2/5 |
| Bsp 2180*** + Psn 24** 60% DDM + 25% Propiconazole | 0.05 + 0.10% | 10/10 | 10/10 | 10/10 | 10/10 | 9/10 | 8/9 | 7/8 | 5/7 | 5/5 |
| Bsp 2180*** + Psn 24** 60% DDM + 25% Propiconazole | 0.05 + 0.14% | 10/10 | 10/10 | 10/10 | 10/10 | 10/10 | 10/10 | 10/10 | 10/10 | 10/10 |

*G = Grain side of leather; F = Flesh side of leather;
**Psn 24 available from Buckman Laboratories, Inc., contains 25% Propiconazole;
***Busperse 2180, available from Buckman Laboratories, Inc., contains 60% DDM

Example 8

Application of Combinations of Propiconazole, Dodecyl Morpholine and Sodium 2-Mercaptobenzothiazole (Na-2-MBT) in the Treatment of Leather Treatment Method Several dilutions of formulations containing propiconazole, as the active ingredient, the potentiator dodecylmorpholine (DDM), and a microbicide sodium 2-mercaptobenzothiazole (Na-2-MBT) were investigated with respect to their ability to prevent the formation of fungi in leather. As a control, the formation of fungi in untreated (i.e. no formulation treatment) leather was observed.

Pre-pickled hides were placed in a drum to which was then added water having a temperature of 78–82° F. and 6% sodium chloride (NaCl). The drum was started and allowed to run for 15 minutes. Next 0.3% formic acid diluted 1:10 in water was added to the drum which was then run for 30 minutes. Afterwards, 0.8% sulfuric acid diluted 1:15 in water was added to the drum. After running the drum for 2.5 hours, the drum was stopped and the pH of the float was taken and found to be between 1.8–2.2. The color of the cut of the leather was also checked with Bromocresol Green dye which ideally was yellow to very light green. Next a solution of 3% CHROMOSAL B (available from Bayer Co. containing 25% $Cr_2O_3$ and having 33% basicity) was added to the drum. Once the drum was started, a formulation containing propiconazole, dodecyl morpholine, and sodium 2-mercaptobenzothiazole was then added. After 3 hours, 5% BAYCHROME A (available from Bayer Co. containing 23% $Cr_2O_3$ and having 66% basicity) was added to the drum which was then allowed to run overnight. Next the chrome penetration in the hides was evaluated visually. If chrome penetration was not sufficient, the drum was allowed to run for a longer period of time until sufficient chrome penetration was achieved. Once achieved, a basification process was begun by very slowly adding a solution of 1.7% sodium bicarbonate to the drum of which the heaters were turned on to increase the temperature within the drum. The sodium bicarbonate addition was added at such a rate as to not be completed under an hour. After sodium bicarbonate addition was complete, the drum was then run for 4 hours. After 4 hours, the pH of the float was checked. If the pH was between 3.65 and 3.85, the float was drained and the leather was washed with cold water. If the pH was lower than 3.65, additional sodium bicarbonate was added and the drum was run for another hour. The pH was again tested. If the pH was still too low, the process of adding sodium bicarbonate and running the drum was repeated until the pH fell within the desired range of 3.65–3.85.

Evaluation Method

Once a week for nine weeks, leather having been treated with propiconazole/dodecyl morpholine/sodium 2-mercaptobenzothiazole combination was evaluated for growth of fungi. Evaluations were made for both the grain and the flesh surface of the leather based on the following scale:

| | |
|---|---|
| 10 | No Growth |
| 9 | |
| 8 | Slight Growth |
| 7 | |
| 6 | Medium Growth |
| 5 | |
| 4 | Moderately Heavy Growth |
| 3 | |
| 2 | Heavy Growth |
| 1 | |
| 0 | Completely Covered |

TABLE 8

Evaluation of Leather Subjected to Tropical Chamber After Treatment with Propiconazole/Dodecyl Morpholine (DDM)/sodium 2-mercaptobenzothiazole (Na-2-MBT)

| Main Components in Formulation | Dosage (%) | Dodecyl Morpholine (DDM) | | | | | | | | |
|---|---|---|---|---|---|---|---|---|---|---|
| | | 1 Week G/F* | 2 Week G/F* | 3 Week G/F* | 4 Week G/F* | 5 Week G/F* | 6 Week G/F* | 7 Week G/F* | 8 Week G/F* | 9 Week G/F* |
| Control - No treatment | 0 | 10/10 | 9/10 | 8/8 | 5/6 | 0/0 | 0/0 | 0/0 | 0/0 | 0/0 |
| 40% Na-2-MBT**, | 0.060% | 10/10 | 10/10 | 10/10 | 10/10 | 10/10 | 10/10 | 10/10 | 10/10 | 10/10 |
| 50% Busan 1298***, | 0.100% | 10/10 | 10/10 | 10/10 | 10/10 | 9/9 | 9/9 | 8/9 | 8/8 | 8/8 |
| 5% Busperse 2280****, 5% DPM***** | 0.120% | 10/10 | 10/10 | 10/10 | 10/10 | 10/10 | 10/10 | 10/10 | 10/10 | 10/10 |
| Control - No treatment | 0 | 10/10 | 0/0 | 0/0 | 0/0 | 0/0 | 0/0 | 0/0 | 0/0 | 0/0 |
| 40% Na-2-MBT**, | 0.060% | 10/10 | 10/10 | 10/10 | 9/10 | 9/9 | 8/8 | 7/7 | 5/5 | 5/5 |
| 50% Busan 1298***, | 0.100% | 10/10 | 10/10 | 10/10 | 10/10 | 10/10 | 10/10 | 10/10 | 10/10 | 10/10 |
| 5% Busperse 2280****, 5% DPM***** | 0.120% | 10/10 | 10/10 | 10/10 | 10/10 | 10/10 | 10/10 | 10/10 | 10/10 | 10/10 |

*G = Grain side of leather; F = Flesh side of leather;
**contains 50% Na-2-MBT;
***Busan 1298, available from Buckman Laboratories, Inc., contains 10% propiconazole;
****Busperse 2280, available from Buckman Laboratories, Inc., contains 80% formic acid salt of DDM;
*****DPM is dipropylene glycol monomethylether.

The claimed invention is:

1. A method to increase the effectiveness of a microbicide comprising the step of applying to a substrate or aqueous system subject to the growth of microorganisms a combination of propiconazole and N-dodecyl morpholine, wherein the N-dodecyl morpholine is present in an amount effective to increase the microbicidal activity of the propiconazole.

2. A microbicidal composition comprising:
   (a) propiconazole, and
   (b) N-dodecyl morpholine
wherein (a) and (b) are present in a combined amount effective to control the growth of at least one microorganism.

3. A microbicidal composition according to clam 2, wherein the microorganism is selected from algae, fungi, and bacteria.

4. A method for controlling the growth of microorganisms on a substrate comprising the step of contacting a substrate susceptible to the growth of microorganisms with a microbicidal composition comprising:
   (a) propiconazole, and
   (b) dodecyl morpholine
and wherein (a) and (b) are present in a combined amount effective to control the growth of at least one microorganism on the substrate.

5. A method according to claim 4, wherein the microorganism is selected from the group consisting of algae, fungi, and bacteria.

6. A method for controlling the growth of microorganisms in an aqueous system capable of supporting growth of a microorganism comprising the step of treating the aqueous system with a micorbicidal composition comprising:
   (a) propiconazole, and
   (b) dodecyl morpholine
and wherein (a) and (b) are present in a combined amount effective to control the growth of at least one microorganism.

7. A method according to claim 6, wherein the microorganism is selected from the group consisting of algae, fungi, and bacteria.

8. A method for controlling the growth of microorganisms on pulp or paper in a papermaking process, comprising the step of contacting the pulp or paper with:
   (a) propiconazole, and
   (b) dodecyl morpholine
and wherein (a) and (b) are present in a combined amount effective to control the growth of at least one microorganism.

9. A method according to claim 8, wherein the microorganism is selected from the group consisting of algae, fungi, and bacteria.

* * * * *